United States Patent
Danielsson et al.

(10) Patent No.: US 6,799,569 B2
(45) Date of Patent: Oct. 5, 2004

(54) DEVICE FOR COMPRESSION OF THE NECK SPINE FOR MEDICAL IMAGING PURPOSES

(76) Inventors: Barbro Danielsson, Almvägen 28, 437 40 Lindome (SE); Thomas Nicklasson, Kuttervägen 39, 439 35 Onsala (SE); Jan A. G. Willen, Krikonvägen 19, 435 43 Mölnlycke (SE)

(*) Notice: Subject to any disclaimer, the term of this patent is extended or adjusted under 35 U.S.C. 154(b) by 0 days.

(21) Appl. No.: 10/161,179

(22) Filed: Jun. 3, 2002

(65) Prior Publication Data

US 2003/0023158 A1 Jan. 30, 2003

(51) Int. Cl.$^7$ ................................................ A61F 5/24
(52) U.S. Cl. ........................ 128/97.1; 602/19; 602/32
(58) Field of Search ............................. 128/97.1, 848, 128/857, 858, 859; 602/32–40, 19; 606/130

(56) References Cited

U.S. PATENT DOCUMENTS

| | | | | |
|---|---|---|---|---|
| 3,925,822 A | * | 12/1975 | Sawyer ............................ | 2/3 |
| 4,688,780 A | | 8/1987 | Hanz | |
| 4,979,519 A | | 12/1990 | Chavarria et al. | |
| 4,995,378 A | * | 2/1991 | Dyer .............................. | 128/75 |
| 5,272,770 A | * | 12/1993 | Allen .............................. | 2/2 |
| 5,810,006 A | | 9/1998 | Votruba et al. | |
| 5,893,365 A | * | 4/1999 | Anderson .................... | 128/848 |
| 5,991,651 A | | 11/1999 | LaBarbera | |
| 6,173,201 B1 | * | 1/2001 | Front ......................... | 606/130 |

FOREIGN PATENT DOCUMENTS

| | | |
|---|---|---|
| DE | 43 18 134 | 12/1994 |
| DE | 197 08 707 | 8/1998 |
| WO | WO 98/17177 | 4/1998 |

* cited by examiner

Primary Examiner—Michael A. Brown
(74) Attorney, Agent, or Firm—Gauthier & Connors LLP

(57) ABSTRACT

The present invention relates to a device for compression of the neck spine for medical imaging purposes, in particular for diagnostic purposes at complementary examination using computed tomography or magnetic resonance tomography, whereby the device comprises a waist arrangement to be placed around and in firm contact with the upper body of a patient, a helmet arrangement to be placed around and in firm contact with the head of the patient, strings connecting said waist arrangement and said helmet arrangement, which strings can be strained independently of each other and comprise each a tension meter to monitor the force by which the strings are stretched.

4 Claims, 1 Drawing Sheet

DEVICE FOR COMPRESSION OF THE NECK SPINE FOR MEDICAL IMAGING PURPOSES

DESCRIPTION

Technical Field

Figure 1:
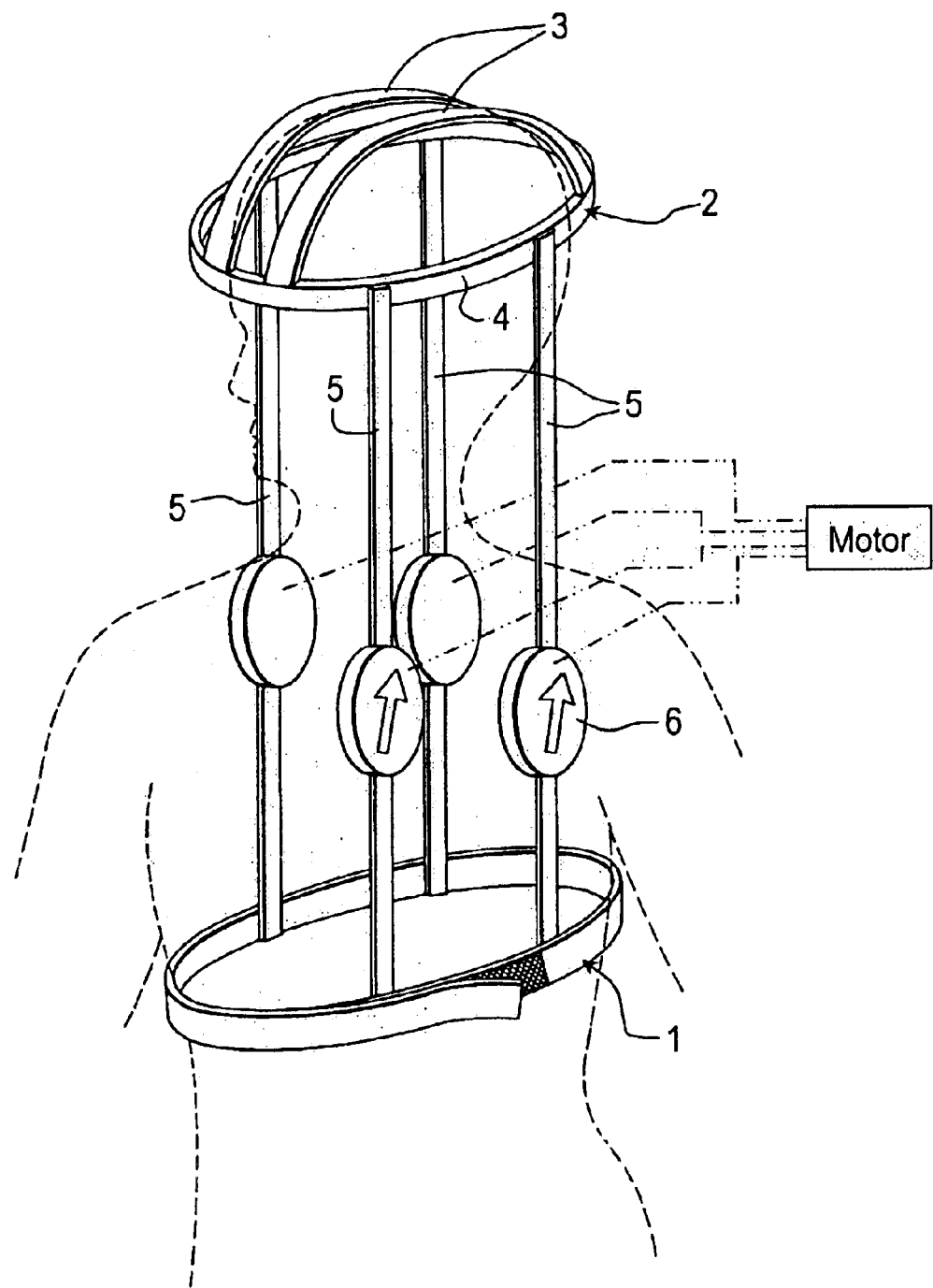

The present invention relates to a device for compression of the neck spine for medical imaging purposes, in particular for diagnostic purposes at complementary examination using computed tomography or magnetic resonance tomography.

The object of the present invention is to obtain a device the use of which provides an aid for an adequate and reproducible examination of the neck spine under load in connection with computed tomography and/or magnetic resonance tomography, in particular for the diagnosis of degenerative and inflammatory conditions as well as degenerative instability in the neck.

BACKGROUND OF THE INVENTION

Diagnosis of the neck with regard to degenerative and inflammatory conditions as well as degenerative instability are hard to carry out under well-defined conditions and the market does not recognise any such diagnostic tools or equipment for said purpose.

EP 95920357.1 discloses a device for compression of the lumbar spine for medical imaging purposes, and then in particular for the diagnosis of the spinal cord canal and nerve structures (spinal stenosis) present.

Further, it is previously known from U.S. Pat. No. 3,629,581 a device for positioning a patients shoulders in connection with an X-ray examination of the spine of a patient, whereby the upper spinal column is pressed downwards towards the examination table and makes it possible to obtain good X-ray pictures of the upper vertebras. Hereby a pressure is applied over the spinal column of the lying patient via two flexible strings provided with handles for the patient which strings are arranged around a foot plate.

There is thus a problem to be solved, viz. to obtain an apparatus or device for the diagnosis of the neck with regard to degenerative and inflammatory conditions as well as degenerative instability under well-defined conditions.

DESCRIPTION OF THE PRESENT INVENTION

It has now surprisingly been shown possible to be able to solve this problem by the present invention which is characterized in that the device comprises a waist arrangement to be placed around and in firm contact with the upper body of a patient, a helmet arrangement to be placed around and in firm contact with the head of a patient, strings connecting said waist arrangement and said helmet arrangement, which strings can be stretched independently of each other and comprise each a tension meter to monitor the force by which the strings are stretched.

By means of the present invention a controlled load of the neck spine can be obtained when the waist arrangement applied around a patient's upper body and the helmet arrangement is placed around and over the head and the strings are stretched to a certain load. Further, the load can be applied asymmetric as well, whereby the neck spine can be examined and diagnosed in any bent position, such as forward, backward, and sidewise.

The invention will now be described more in detail with reference to the attached drawing, showing a preferred device of the invention, however, without being restricted thereto, wherein FIG. 1 shows a lateral view of one embodiment of a device according to the present invention.

1 denotes a waist coat arrangement which is arranged to be placed around the upper body of a patient, the thoracic region, and secured up to the armpit, whereby it is fastened conveniently using cords of the burdock type. The waist coat arrangement is applied firmly but still comfortably, but in such a manner that it does not slide over the body. A helmet 2 is provided with means to have it arranged firmly and non-slidable onto a head. The helmet 2 is generally of the type having a number of cords 3 passing over the skull and a skull band 4 which is adjustable as to the diameter of the head to be used on. Between the helmet and the waist coat arrangement there are at least four pulling cords or strings 5 arranged, whereby each string individually can be disconnected/connected to the helmet/waist coat arrangements. Each string comprises a tension meter 6 and a straining means arranged in such a way that each string can be stretched individually, whereby the tension in each string can be monitored. The straining means can, in a simple embodiment, be a mechanical rolling device, manually or motor driven. The tension meters 6 are preferably of an electronic type so that they can be attached to a computer for collecting data necessary to determine and document the conditions used.

The patient provided with the device of the invention is placed upon a resting surface of a patient table being suitable for being introduced in a device for computed tomography or magnetic resonance tomography. Computed tomography and magnetic resonance tomography are known units and are subject of the present invention.

By having at least four cords or stings 5 the different bending conditions can be achieved. During normal examination the tension in the cords will be about 8 to 10 kpm, whereby under certain extreme conditions it may be as high as 15 to 20 kpm or even higher, e.g. when studying a whiplash damage, where the neck has been subject to very high forces and loads. The number of cords can be increased if more specific bending conditions will be achieved. In such cases six or eight cords or strings with their respective tension meters can be attached.

The tension meters 6 may also be connected to a motor which affects the straining of the cords 5 whereby a predetermined, adjusted value can be maintained as the tension meters 6 control the motor.

At an examination a patient is placed on his back on the resting surface of the patient table of a tomography apparatus the waist coat arrangement is arranged around the thorax and the helmet arrangement is arranged to the head of the patient, whereafter the cords or strings with their respective tension meters are attached between the two arrangements. The cords or strings are strained to a predetermined value, and the patient is brought into the tomography apparatus to obtain the pictures wanted. To determine conditions using a magnetic resonance tomograph certain special accessories can be needed to obtain the right signals due to a distance between the signal receiving parts and the patient. However, this is common knowledge to the operator of such tomographs, and is not part of the invention.

What is claimed is:

1. A device for compression of the neck spine for medical imaging purposes, in particular for diagnostic purposes at complementary examination using computed tomography or magnetic resonance tomography, wherein the device comprises a waist arrangement to be placed around and in firm contact with the upper body of a patient, a helmet arrangement to be placed around and in firm contact with the head of a patient, strings connecting said waist arrangement and said helmet arrangement, which strings can be strained independently of each other and comprise each a tension meter to monitor the force by which the strings are stretched.

2. A device according to claim 1, wherein the straining force of the strings is arranged to be regulated manually.

3. A device according to claim 1, wherein the straining force of the strings is arranged to be regulated using a motor.

4. A device according to claim 1, wherein the straining force of the strings is arranged to be regulated using a motor controlled by said tension meters.

\* \* \* \* \*